United States Patent [19]

Rork et al.

[11] Patent Number: 5,582,838
[45] Date of Patent: Dec. 10, 1996

[54] CONTROLLED RELEASE DRUG SUSPENSION DELIVERY DEVICE

[75] Inventors: Gerald S. Rork; James D. Pipkin, both of Lawrence, Kans.

[73] Assignee: Merck & Co., Inc., Rahway, N.J.

[21] Appl. No.: 363,451

[22] Filed: Dec. 22, 1994

[51] Int. Cl.[6] .............................. A61K 9/24; A61K 9/32; A61K 9/36
[52] U.S. Cl. .................. 424/472; 424/471; 424/473; 424/479; 424/480; 424/482; 424/470
[58] Field of Search ................................ 424/472, 473, 424/471, 470, 479, 480, 482

[56] References Cited

U.S. PATENT DOCUMENTS

| | | | |
|---|---|---|---|
| 3,146,169 | 8/1964 | Stephenson et al. | 167/82 |
| 3,538,214 | 11/1970 | Polli et al. | 424/19 |
| 3,845,770 | 11/1974 | Theeuwes et al. | 128/260 |
| 3,916,899 | 11/1975 | Theeuwes et al. | 128/260 |
| 3,957,523 | 5/1976 | Ohno et al. | 106/189 |
| 4,160,452 | 7/1979 | Theeuwes | 128/260 |
| 4,200,098 | 3/1980 | Ayer et al. | 128/260 |
| 4,218,433 | 8/1980 | Kooichi et al. | 424/15 |
| 4,220,153 | 9/1980 | Dresback et al. | 128/260 |
| 4,235,236 | 11/1980 | Theeuwes | 128/260 |
| 4,244,941 | 1/1981 | Lerk | 424/21 |
| 4,256,108 | 3/1981 | Theeuwes | 128/260 |
| 4,285,987 | 8/1981 | Ayer et al. | 427/3 |
| 4,326,525 | 4/1982 | Swanson et al. | 128/260 |
| 4,327,725 | 5/1982 | Cortese et al. | 128/260 |
| 4,557,925 | 12/1985 | Liadahl et al. | 424/19 |
| 4,578,075 | 3/1986 | Urquhart et al. | 604/892 |
| 4,601,893 | 7/1986 | Cardinal | 424/15 |
| 4,681,583 | 7/1987 | Urquhart et al. | 604/892 |
| 4,687,660 | 8/1987 | Baker et al. | 424/465 |
| 4,743,247 | 5/1988 | Wong | 604/892.1 |
| 4,783,337 | 11/1988 | Wong et al. | 424/468 |
| 4,814,182 | 3/1989 | Graham et al. | 424/484 |
| 4,839,177 | 6/1989 | Colombo et al. | 424/482 |
| 4,851,228 | 7/1989 | Zentner et al. | 424/456 |
| 4,898,733 | 2/1990 | DePrince et al. | 424/425 |
| 4,915,954 | 4/1990 | Ayer et al. | 424/473 |
| 4,968,507 | 11/1990 | Zentner et al. | 424/465 |
| 4,971,790 | 11/1990 | Magruder et al. | 424/78 |
| 4,994,273 | 2/1991 | Zentner et al. | 424/422 |
| 4,996,060 | 2/1991 | Eckenhoff et al. | 424/473 |
| 5,004,614 | 4/1991 | Staniforth | 424/466 |
| 5,030,452 | 7/1991 | Curatolo | 424/450 |
| 5,057,321 | 10/1991 | Edgren | 424/413 |
| 5,230,895 | 7/1993 | Czarnecki et al. | 424/422 |
| 5,366,738 | 11/1994 | Rork et al. | 424/473 |

FOREIGN PATENT DOCUMENTS

| | | |
|---|---|---|
| 0040457 | 1/1981 | European Pat. Off. . |
| 0378404 | 7/1990 | European Pat. Off. . |
| 0021758 | 1/1981 | United Kingdom . |
| 2116841 | 11/1983 | United Kingdom . |

OTHER PUBLICATIONS

Proceed. Intern. Symp. Control Rel. Bioact. Mater., 20 (1993).
J. Pharm. Sci., 72, pp. 772–775 (1983), by Kallstrand, et al.

Primary Examiner—James M. Spear
Attorney, Agent, or Firm—Francis P. Bigley; Mark R. Daniel

[57] ABSTRACT

A device is disclosed for the controlled delivery of a beneficial agent, the device consisting of (i) a core comprising at least two layers, wherein at least one layer comprises a beneficial agent and a polymer which forms microscopic gel beads upon hydration and at least one layer which comprises a polymer which forms microscopic gel beads upon hydration; and (ii) an impermeable, insoluble coating which adheres to and surrounds the core and contains apertures which provide an area for the hydration and release of the microscopic gel beads.

23 Claims, 4 Drawing Sheets

CONTROLLED RELEASE DRUG SUSPENSION DELIVERY DEVICE

BACKGROUND OF THE INVENTION

This invention pertains to both a useful and novel drug-delivery device for dispensing a drug to an environment of use. Particularly, the invention pertains to a system capable of delivering a pharmaceutically active ingredient in a controlled manner, at near zero order rate. The dosage form consists of a core surrounded by an impermeable, insoluble coating, the coating having apertures which expose selected areas of the core to the environment of use. The composition of the coating is such that hydration of the core ingredients occurs only at the exposed portions of the core. The core is composed of at least two layers. One of these contains a pharmaceutically active compound. At least one other layer which does not contain a pharmaceutically active ingredient is also present. At least one polymer which swells and forms gel-like beads upon hydration is included in each layer of the core.

In the environment of use, biological fluid contacts the exposed portions of the core surface where hydration of the exposed polymer occurs. As the particles of polymer at the exposed surface absorb water, microscopic gel beads result. If the exposed portion of the core contains both a pharmaceutically active compound and microscopic gel bead forming polymer, then as the polymer swells and moves into the environment of use, the pharmaceutically active compound is carried with it. If the exposed portion of the core contains only the polymer then only the polymer moves into the environment of use.

Control of the rate of hydration of the polymer and therefore the rate of delivery of the exposed core ingredients to the environment of use is accomplished by the incorporation of holes or openings in the impermeable, insoluble coating. These holes or apertures expose discrete, predetermined sections of the core surface. Since the exposed portion of the core surface is bounded on all sides by the coating, hydration of the polymer occurs only at the pre-selected, exposed surface of the core. The resulting microscopic gel bead suspension exudes into the environment of use.

The rate of release of the pharmaceutically active ingredient is not dependent upon the solubility of the beneficial agent in the biological fluid. Rather, the release rate is essentially dependent upon the rate at which the microscopic gelatinous beads form at the exposed surface of the device and exude from the device carrying the beneficial agent and any other core excipient materials that are present. Therefore, rate of release may be controlled by controlling the size and number of holes which expose the surface of the core to the environment.

The rate of delivery of the pharmaceutically active ingredient is further dependent on the composition of the core layer exposed at the surface, at a given time. In this way, delayed delivery or intermittent delivery may be achieved by use of a core layer which does not contain the pharmaceutically active ingredient, while at the same time assuring complete delivery of the pharmaceutically active ingredient.

The need for systems that can deliver both soluble and insoluble pharmaceutically active ingredients, at a constant rate, over a four to twenty-four hour period is well established. Further, the need for a device which is capable of a programmed, delayed start of delivery is also well recognized.

Several approaches to this problem have been proposed. The existing technology relies predominantly on diffusion controlled systems which are effective only when soluble active agents are dispensed. A further limitation of osmotic systems lies in the requirement that the osmogent must dissolve in the presence of the swellable polymer any inadvertent interaction between the osmogent and the polymer can result in an unpredicted change in the rate of release of the pharmaceutically active ingredient.

Dosage forms that rely upon the establishment of an extra device superstructure have also been disclosed. However, these can be damaged during in vivo transit, for example, in the gastrointestinal tract. If portions of the superstructure break away greater surface area than desired will be exposed to the environment of use and unpredictable release of the active agent may result.

U.S. Pat. No. 4,814,182 discloses the use of rods or slabs of pre-hydrated and swelled polyethylene oxide hydrogel. The polymer is impregnated with a biologically active agent during a hydration procedure. The hydrated polymer is then dried and partially coated with an impermeable, insoluble material. When placed in an aqueous environment, the polymer swells but does not dissolve or disintegrate. The entrapped active ingredient is released from the polymer by diffusion. The mechanism of release is based on the ability of the soluble drug to diffuse through the rehydrated hydrogel and move into the aqueous environment.

U.S. Pat. No. 4,839,177 discloses the use of hydrogels compressed to defined geometric forms that are admixed with biologically active ingredients where a portion of the device is affixed to a "support platform" made of an insoluble polymeric material. When hydrated, the swellable, gellable hydrogel expands beyond the device and establishes a superstructure from which the active agent is released either by diffusion, if the active agent is soluble, or by erosion, if the active agent is insoluble. The generation and maintenance of the superstructure is vital to the success of this device.

An osmotic dosage form which utilizes a semipermeable wall containing at least one "exit means" which passes through the wall, surrounding a core containing an osmotic agent, a neutral and ionizable hydrogel and an active ingredient is disclosed in U.S. Pat. No. 4,971,790. The coating of this device is permeable to water from the environment of use. Water moves into the core through the semipermeable membrane. Once inside the device, the water solubilizes the osmotic agent and ionizable hydrogel. Pressure builds up inside the device, due to the ionization of the osmogent. Ultimately, the solubilized, ionizable hydrogel, containing the beneficial agent, the neutral hydrogel and other core excipients are pumped out of the core, through an exit means and into the environment of use.

U.S. Pat. No. 4,915,954 discloses a device having a two layer core. One layer is faster releasing than the other and is primarily composed of a mixture of hydroxypropyl cellulose and hydroxypropylmethyl cellulose. The lower layer can also be made up of cellulosic polymers but of different or higher molecular weight. This slower layer may also contain a hydrogel, preferably polyethylene oxide. This device requires a semipermeable wall. The need to control wall thickness (or weight of wall) and its effect on permeability and subsequently on release is shown in example 4 and FIG. 7 of the disclosure. Control of wall thickness is one of the major negative features of osmotically controlled delivery devices.

European Application 0 378 404 A2 discloses a microporous coating on a hydrogel osmotic core. This device comprises a coating through which the pharmaceutically active agent may pass when the device is exposed to an aqueous environment. Like the other devices discussed, wetting, hydration or solubilization of the core material by the inhibition of fluid through the coating must occur for this device to function.

U.S. Pat. No. 5,366,738 discloses a device which consists essentially of a homogeneous compressed core prepared from an admixture comprising a therapeutically effective amount, of a pharmaceutically active ingredient and a polymer, which forms microscopic gelatinous beads upon hydration. This core is coated with a water insoluble, water impermeable polymeric coating, which surrounds and adheres to the core, the coating having a plurality of apertures, exposing between about 5 and about 75% of the core surface. While this dosage forms provides a means for controlling release of an insoluble pharmaceutically active ingredient, delayed delivery is not provided.

The usefulness of the above devices would be increased if a device and method were provided to improve the release of pharmaceutically active ingredients, at a constant rate, and if a means for delaying release of the pharmaceutically active ingredient was also possible. Further improvement would be realized if a dosage form was provided that provides for intermittent delivery of the pharmaceutically active ingredient.

SUMMARY OF THE INVENTION

A drag delivery device is disclosed for the controlled in situ production and release of a suspension containing a beneficial agent, consisting essentially of:

(A) a compressed core which comprises at least two layers, wherein at least one layer comprises an admixture of a therapeutically effective amount for those in need thereof, of a pharmaceutically active ingredient and a polymer which upon hydration forms microscopic gelatinous beads; and at least one other layer comprising a polymer which upon hydration forms microscopic gelatinous beads; and (B) a water insoluble, water impermeable polymeric coating, applied to the core which surrounds and adheres to the core, the coating having apertures, exposing between about 5 and about 75% of the core surface.

BRIEF DESCRIPTION OF THE DRAWINGS

FIG. 1 is a schematic representation of one embodiment of the instant invention. The impermeable, insoluble coating (10) completely surrounds the device. Apertures, (11) provide for defined sites where hydration of the core surface occurs, once the dosage form is placed in the environment of use. The core is composed of a central layer (14) and two outer layers (13). Central layer, (14) comprises both the pharmaceutically active ingredient (15) and the polymer (16) which upon hydration swells and forms gelatinous beads. The outer layers of the core (13) contain the polymer (16) but no pharmaceutically active ingredient.

DETAILED DESCRIPTION OF THE DRAWINGS

Figure 1:
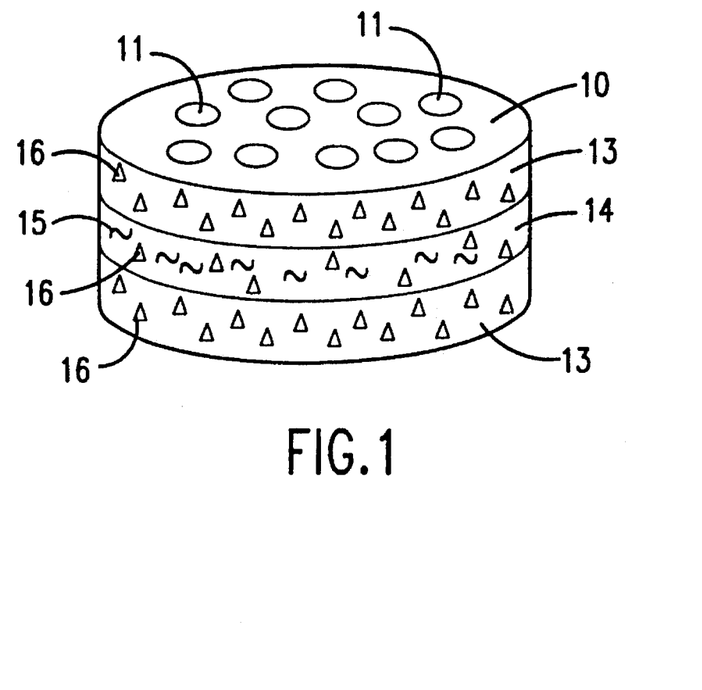

In operation, aqueous solution, from the environment of use, contacts the surface of the core that is exposed within the apertures (11). The available water begins to hydrate the microscopic gel bead forming polymer (16) at the surface of the core. If present, the polymer hydration modulating agent (not shown), at the exposed core surface, is solubilized and establishes the environment required for controlled hydration of the polymer.

As the polymer (16) is hydrated, it exudes from the surface as microscopic gelatinous beads. Ultimately, hydration of the middle layer (14) results in this layer being present at the surface where particles of the beneficial agent (15) are extricated from the surrounding surface. These particles of beneficial agent (15) move from the core surface into the environment of use in a suspension with the microscopic gelatinous beads of hydrated polymer (16).

If apertures are drilled into both sides or faces of the device, hydration may continue from each side simultaneously. In the alternative, when apertures are drilled into one side or face of the device only, hydration first occurs in the outside layer nearest the apertures, then at the central layer (14) and finally at the outside layer furthermost from the apertures. When hydration of this layer occurs, the gelatinous beads of polymer exude from the device through the apertures and in so doing sweep the remaining contents of the middle layer (14) from the core and into the environment of use. This sweeping effect results in an extension of the zero order delivery rate and allows for efficient delivery of the pharmaceutically active ingredient.

Figure 2:
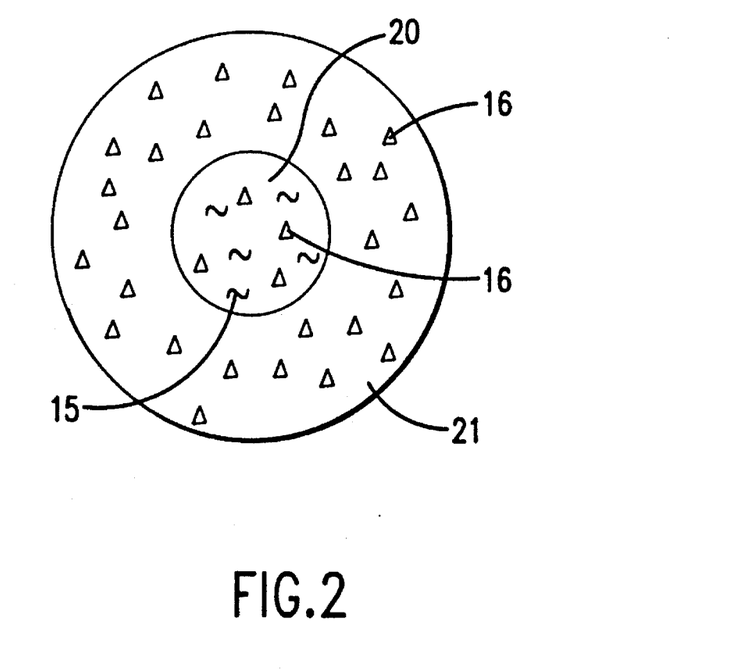
FIGS. 2 and 3 are schematic representations of an additional embodiment of the core of the instant invention where a tablet (20) which contains the pharmaceutically active ingredient (15) and the polymer (16) which upon hydration swells and forms gelatinous beads is compressed within an envelope (21) of inert material which comprises the polymer (16).
Figure 3:
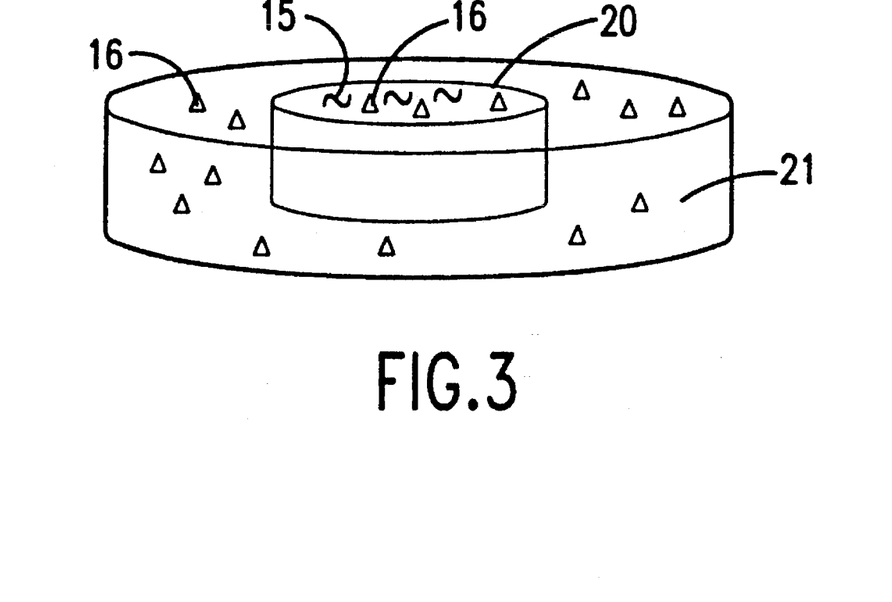
Figure 4:
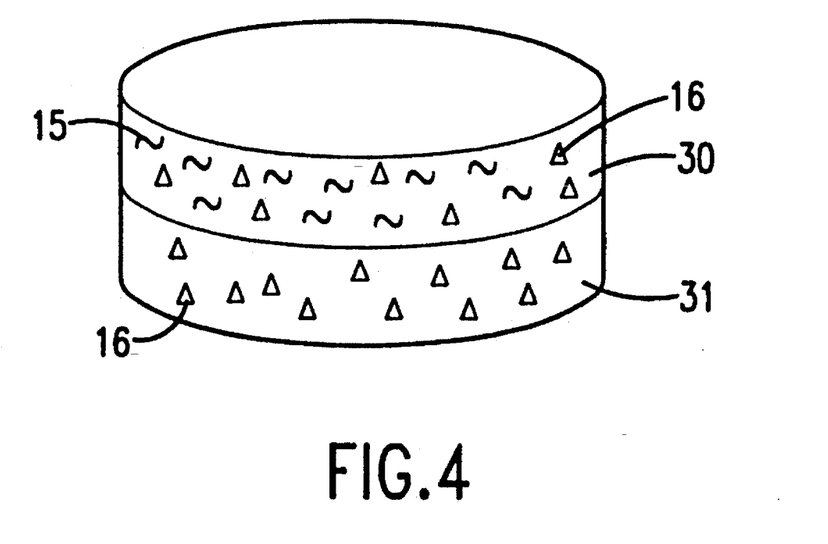
FIG. 4 is a schematic representation of a preferred embodiment of the core of the instant invention where a two layer core is utilized. In this embodiment, one layer of the core comprises both the pharmaceutically active ingredient (15) and the polymer (16), while the other layer of the core comprises the polymer (16).

FIGS. 2, 3 and 4 are defined throughout this document.

Figure 5:
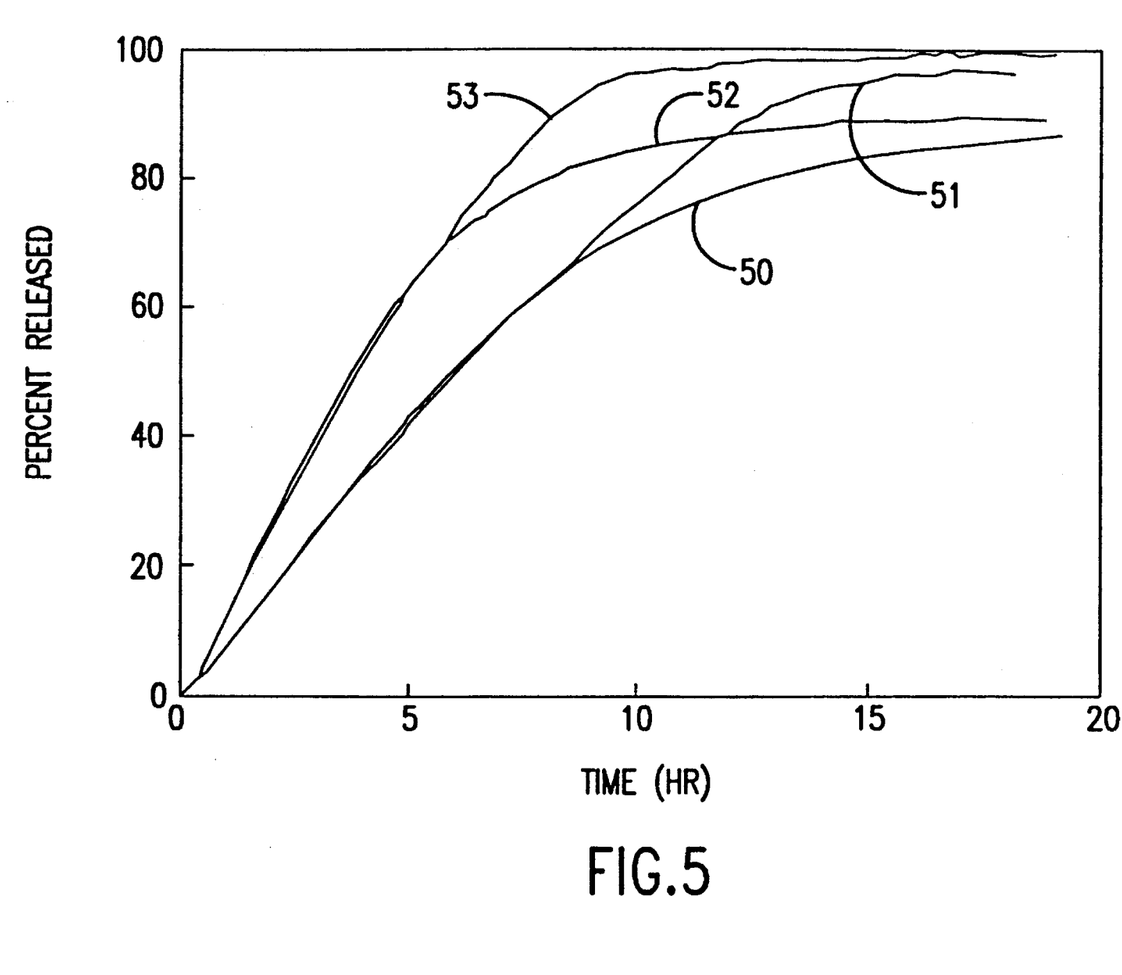
FIG. 5 is a plot of the release of the pharmaceutically active ingredient from two configurations of the instant invention and a comparison to the release from a homogeneous core device having the same number of holes in the coating.

FIG. 5 is a plot of the pharmaceutically active ingredient released over time from two configurations of the instant invention and a comparison to a standard, homogeneous core device with the same hole configuration.

DETAILED DESCRIPTION OF THE INVENTION

The novel drug delivery device of this invention provides for the controlled in situ production and release of a suspension containing a beneficial agent, which comprises:

(A) a compressed core which comprises at least two layers, wherein at least one layer comprises an admixture of a therapeutically effective amount for those in need thereof, of a pharmaceutically active ingredient and a polymer which upon hydration forms microscopic gelatinous beads; and at least one other layer comprising a polymer which upon hydration forms microscopic gelatinous beads; and (B) a water insoluble, water impermeable polymeric coating, which surrounds and adheres to the core, the coating having apertures, exposing between about 5 and about 75% of the core surface.

By "drug delivery device" is meant, a dosage form that provides a convenient means of delivering a pharmaceutically active ingredient or drug to a subject in need thereof. The subject can be a human or any other animal in need of such pharmaceutically active ingredient. The device is designed to be useful for the delivery of a pharmaceutically active ingredient by any pharmaceutically accepted means such as by swallowing, retaining it within the mouth until the beneficial agent has been dispensed, placing it within the bucal cavity, or the like.

By "controlled in situ production" is meant that the rate of release of the pharmaceutically active ingredient, that is the amount of pharmaceutically active ingredient released from the device to the environment of use, follows a predetermined pattern. Thus, relatively constant or predictably varying amounts of the beneficial agent can be dispensed over a specified period of time.

By "pharmaceutically active agent" is meant any compound commonly referred to as a "drug" and its equivalents which includes any physiologically or pharmacologically active substance that produces a localized or systemic effect or effects in animals. The term "animal" includes mammals, humans and primates such as domestic, household, sport or farm animals such as sheep, goats, cattle, horses and pigs, laboratory animals such as mice, rats and guinea pigs, fishes, avians, reptiles and zoo animals.

The pharmaceutically active ingredients that can be delivered by the novel device of this invention, includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine and hormone systems, immunological system, reproductive system, skeletal systems, autocoid systems, alimentary and excretory systems, inhibitory and histamine systems, and those materials that act on the central nervous system such as hypnotics and sedatives.

Examples of pharmaceutically active ingredients are disclosed in *Remington's Pharmaceutical Sciences*, 16th Ed., 1980, published by Mack Publishing Co., Eaton, Pa. and in *The Pharmacological Basis of Therapeutics*, by Goodman and Gilman, 6th Ed., 1980, published by the MacMillan Company, London and in *The Merck Index*, 11th Edition, 1989, published by Merck & Co., Rahway, N.J. The dissolved drug can be in various forms, such as charged molecules, charged molecular complexes or ionizable salts. Acceptable salts include, but are not limited to hydrochlorides, hydrobromide, sulfate, laurylate, palmitate, phosphate, nitrate, borate, acetate, maleate, malate, tromethamine, tartrate, oleate, salicylate, salts of metals, and amines or organic cations, for example quaternary ammonium.

Derivatives of pharmaceutically active ingredients such as esters, ethers and amides without regard to their ionization and solubility characteristics can be used alone or mixed with other compounds. Also, a pharmaceutically active ingredient can be used in a form that upon release from the device, is converted by enzymes, hydrolyzed by body pH or other metabolic processes to the original form, or to a biologically active form. That is, prodrugs are specifically included within the definition of pharmaceutically active ingredients.

Specific examples of pharmaceutically active ingredients that may be adapted for use include, barbiturates such as pentobarbital sodium, phenobarbital, secobarbital, thiopental and mixtures thereof; heterocyclic hypnotics such as dioxopiperidines and glutamides; hypnotics and sedatives such as amides and ureas, exemplified by diethyiisovaleramide and α-bromo-isovaleryl urea; hypnotic and sedative urethanes and disulfanes; psychic energizers such as isocarboxazid, nialamide, imipramine, amitryptyline hydrochloride, pargylene, and protryptyline hydrochloride; tranquilizers such as chloropromazine, promazine, fluphenzaine, reserpine, deserpidine, and meprobamate; benzodiazepines such as diazepam and chlordiazepoxide; anticonvulsants such as primidone, phenytoin, and ethosuximide; muscle relaxants and antiparkinson agents such as mephenesin, methocarbomal, cyclobenzaprine hydrochloride, trihexylphenidyl hydrochloride, levodopa/carbidopa, and biperiden; antihypertensives such as α-methyldopa and the pivaloyloxyethyl ester of α-methyldopa; calcium channel blockers such as nifedipine, diltiazem hydrochloride, diltiazem malate and verapamil hydrochloride; analgesics such as morphine sulfate, codeine sulfate, meperidine, and nalorphine; antipyretics and antiinflammatory agents such as aspirin, indomethacin, ibuprofen, sodium indomethacin trihydrate, salicylamide, naproxen, colchicine, fenoprofen, sulindac, diflunisal, diclofenac, indoprofen and sodium salicylamide; local anesthetics such as procaine, lidocaine, tetracaine and dibucaine; antispasmodics and muscle contractants such as atropine, scopolamine, methscopolamine, oxyphenonium, papaverine; prostaglandins such as $PGE_1$, $PGE_2$, $PGF_{2a}$; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-aminoquinolines and pyrimethamine; hormonal and steroidal agents such as dexamethasone, prednisolone, cortisone, cortisol and triamcinolone; androgenic steroids such as methyltestosterone; estrogenic steroids such as 17α-estradiol, α-estradiol, estriol, α-estra-diol 3-benzoate, and 17-ethynyl estradiol-3-methyl ether; progestational steroids such as progesterone; sympathomimetic drugs such as epinephrine, phenylpropanolamine hydrochloride, amphetamine, ephedrine and norepinephrine; hypotensive drugs such as hydralazine; cardiovascular drugs such as procainamide hydrochloride, amyl nitrite, nitroglycerin, dipyridamole, sodium nitrate and mannitol nitrate; diuretics such as chlorothiazide, acetazolamide, methazolamide, hydrochlorothiazide, amiloride hydrochloride and flumethiazide, sodium ethacrynate, and furosemide; an tiparasitics such as bephenium, hydroxynaphthoate, dichlorophen and dapsone; antineoplastics such as mechlorethamine, uracil mustard, 5-fluorouracil, 6-thioguanine and procarbazine; β-blockers such as pindolol, propranolol, metoprolol, oxprenolol, timolol maleate, atenolol; hypoglycemic drugs such as insulin, isophane insulin; protamine zinc insulin suspension, globin zinc insulin, extended insulin zinc suspension, tolbutamide, acetohexamide, tolazamide and chlorpropamide; antiulcer drugs such as cimetidine, ranitidine, famotidine and omeprazole nutritional agents such as ascorbic acid, niacin, nicotinamide, folic acid, choline, biotin, pantothenic acid; essential amino acids; essential fats; ophthalmic drugs such as timolol maleate, pilocarpine nitrate, pilocarpine hydrochloride, atropine sulfate, scopolamine; electrolytes such as calcium gluconate, calcium lactate, potassium chloride, potassium sulfate, sodium fluoride, ferrous lactate, ferrous gluconate, ferrous sulfate, ferrous fumurate and sodium lactate; and drugs that act on α-adrenergic receptors such as clonidine hydrochloride; alnalgesic drugs such as acetaminophen, oxycodone, hydrocodone, and propoxyphene; antihypercholesterolemic drugs such as simvastatin, pravastatin, lovastatin and genfibrozil; antiinfective drugs such as cefoxitin, cefazolin, cefotaxime, ciprofloxacin, cephalexin, norfloxacin, amprolium, ampicillin, amoxicillin, cefacloi, erythromycin, nitrofurantoin, minocycline, doxycycline, cefadroxil, miconazole, clotrimazole, phenazopyridine, clorsulon, fludalanine, pentizidone, cilastin, phosphonomycin, imipenem; gastrointestinal drugs such as bethanechol, clidinium, dicyclomine, meclizine, prochlorperizine, trimethobenzamide, loperamide, diphenoxylate, and metoclopramide; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim, and ivermectin.

The above list of drugs is not meant to be exhaustive. Many other drags will certainly work in the instant invention.

By "compressed core which comprises at least two layers" is meant that an admixture of ingredients comprising a beneficial agent, a polymer which produces microscopic gel beads when hydrated, and other ingredients that may affect any of (1) the rate of production of the suspension (2) the stability of the components of the dosage form or (3) the mixing or compression characteristics of the admixture, are blended in such a way to produce a uniform product. This uniform product is then pressed, within a die, to produce a desired form, normally in the shape of a tablet. This pressed product constitutes at least one layer of the compressed core.

Further a second admixture of ingredients comprising a polymer which produces microscopic gel beads when hydrated, and other ingredients that may affect any of (1) the rate of production of the suspension (2) the stability of the components of the dosage form or (3) the mixing or compression characteristics of the admixture, are blended in such a way to produce a uniform product. This uniform product is then pressed, within a die, to produce a desired form, normally in the shape of a tablet. This pressed product constitutes at least one additional layer of the compressed core.

The "compressed core which comprises at least two layers" may be produced manually or using automated equipment as described herein.

In addition, the "compressed core which comprises at least two layers" may be produced using a multilayer tablet press such as those produced by Manesty Machines Limited.

The "compressed core" may have more than two layers. In an embodiment of this invention, the compressed core is made of three layers. The middle layer contains both the pharmaceutically active ingredient and a polymer which upon hydration forms microscopic gelatinous beads, as well as other excipients useful in the production, dissolution and delivery of the layer. A top and bottom layer, which are adjacent to and above and below the middle layer, each contain a polymer which, upon hydration, forms microscopic gelatinous beads, as well as other excipients useful in the production, dissolution and delivery of the layer are also present in this preferred embodiment.

In this configuration both the top and bottom of the core, which are also known as the upper or lower face of the core, are identical. As a result, when, as in the preferred embodiment, apertures or holes are drilled in only one side of the core, the exact orientation of the core does not need to be considered. That is, since both the top and bottom of the core are identical, the apertures can be drilled in either face without regard to the orientation of the tablet. This results in faster processing of the device during the drilling process and also introduces a programmed lag time into the delivery of the pharmaceutically active compound.

The compressed core contains a "therapeutically effective amount" of beneficial agent and a polymer which upon hydralion results in microscopic gel beads. By "therapeutically effective amount" is meant that the quantity of pharmaceutically active ingredient which has been demonstrated to be sufficient to induce the desired effect during studies utilizing the compound.

Other excipients such as lactose, magnesium stearate, microcrystalline cellulose, starch, stearic acid, calcium phosphate, glycerol monostearate, sucrose; polyvinylpyrrolidone, gelatin, methylcellulose, sodium carboxymethylcellulose, sorbitol, mannitol, polyethylene glycol and other ingredients commonly utilized as stabilizing agents or to aid in the production of tablets may also be present in the layers of the core.

The pharmaceutically active ingredient may be in a layer of the core as a dispersion, particle, granule, or powder. Also, the pharmaceutically active ingredient may be mixed with a binder, dispersant, emulsifier or wetting agent and dyes.

The pharmaceutically active ingredient may comprise from about 0.01% to about 75% of the core weight. Generally, the delivery device can house from about 0.05 ng to about 5 grams of active agent or more, with individual devices containing, for example, 25 mg, 1 mg, 5 mg, 250 mg, 500 mg, 1.5 g, or the like.

The "polymer which upon hydration forms gelatinous micro beads" useful in the novel device of this invention broadly encompasses any polymer that upon hydration, is capable of producing discrete microscopic gel beads which support a suspension, including the beneficial agent, as it forms. The gel forming polymer used also must exude from the core surface in such a way that the beneficial agent is carded into the environment of use. Upon hydration, the gelatinous micro beads must be predisposed to leave the surface taking the drug with it. This assures a constant surface area exposed to the solvent of the environment of use and maintains the appropriate rate of release.

The "microscopic gelatinous beads" are composed of discrete particles of hydrated polymer. Both size and hydration rate of these microscopic gel beads are characteristics of the individual polymers. Illustrative of this type of polymer are "AQUAKEEP J-550", "AQUAKEEP J-400", which are trade names for sodium acrylate polymer produced by Seitetsu Kagaku Co., Ltd., Hyogo, Japan. The "AQUAKEEP" polymers are generically described in U.S. Pat. No. 4,340,706. Also illustrative of this type of polymer are the carboxypolymethylenes prepared from acrylic acid cross-linked with allyl ethers of sucrose or pentaerythritol and sold under the trade names "CARBOPOL 934P" and "CARBOPOL 974P" which are trade names for two carbamer type polymers produced by B.F. Goodrich Chemical Company, Cleveland, Ohio. Carbamer polymers are generically described in U.S. Pat. No. 2,909,462 and in the National Formulary XVII at p. 1911, CAS Registry Number 9003-01-4. All of the forgoing references are hereby incorporated by reference.

In the dry state, "CARBOPOL 974P" and "CARBOPOL 934P" particles range in size from 2 to 7 microns. When these particles are hydrated, microscopic gel beads in the range of 20 microns are produced. When "AQUAKEEP J-550" or "AQUAKEEP J-400" particles are hydrated, microscopic gel bead diameter can range in size from 100 to 1000 microns.

The "polymer hydration modulator" useful in the novel device of this invention broadly encompasses any water soluble compound that can inhibit or enhance the rate of hydration of the gel forming polymer of the core. Among the groups of compounds that can exert this effect are acids, bases, and the salts of acids and bases such as adipic acid, citric acid, fumaric acid, tartaric acid, succinic acid, sodium carbonate, sodium bicarbonate, betamine hydrochloride, sodium citrate, arginine, meglamine, sodium acetate, sodium phosphates, potassium phosphates, calcium phosphate, ammonium phosphate, magnesium oxide, magnesium hydroxide, sodium tartrate and tromethamine. Other compounds that can be used as polymer hydration modifiers include sugars such as lactose, sucrose, mannitol, sorbitol, pentaerythritol, glucose and dextrose. Polymers such as microcrystalline cellulose and polyethylene glycol as well as surfactants and other organic and inorganic salt can also be used to modulate polymer hydration.

The hydration modulating agents are solubilized by the aqueous media of the environment and establish an environment such that the pH, ionic strength or hydrophilic character is appropriate for the desired polymer microscopic gel bead hydration rate. For example, these hydration modulating agents can enhance or retard the neutralization of acidic functional groups on the polymer which affects the rate of hydration.

The core compartment containing the drug, hydration modulator, and microscopic gel bead polymer as described herein, is typically in the form of a solid conventional tablet. The layers of the core may contain compressing aids and diluents such as lactose that assist in the production of compressed tablets. The layers of the core may be comprised of a mixture of agents combined to give the desired manufacturing and delivery characteristics. The number of agents that may be combined to make the core is substantially without an upper limit with the lower limit equaling two components: the gel forming polymer and the beneficial agent.

The preferred specifications for the pharmaceutically active ingredient containing layer of the core is summarized as follows:

1. Core Drug Loading (size): 0.01% to 75% by weight of the total core mass or 0.05 nanogram to 5 grams or more (includes dosage forms for humans and animals).

2. Polymer Hydration Modulator: 0% to 75% by weight of the total core mass.

3. Gel Forming Polymer: 5 to 75% by weight of the total core mass.

The preferred specifications for the layer which does not contain a pharmaceutically active ingredient is summarized as follows:

1. Gel Forming Polymer: 5 to 75% by weight of the total core mass.

2. Polymer Hydration Modulator: 0 to 75% by weight of the total core mass.

In an other preferred embodiment of the core of this invention, a tablet which comprises the pharmaceutically active ingredient and the gel forming polymer is first compressed, and then inlayed into a larger outer inert tablet which comprises the gel forming polymer but no pharmaceutically active agent. This results in a device which comprises an inner tablet compressed into an inert envelope of the gel forming polymer exposing one face of the inner tablet. This embodiment is shown in FIGS. 2 and 3.

FIG. 2 is a top view of the finished dosage form where the inner tablet (20) which comprises both the pharmaceutically active ingredient and the gel forming polymer and the larger inert outer tablet envelope (21) is shown. FIG. 3 shows a side view of the same embodiment, and it can be seen that one face (22) of the inner tablet (20) is exposed to the ambient environment while the edges (23) and remaining face (24) of the inner tablet (20) are surrounded by the larger inert outer tablet (21).

Inlaid tablets of this type can be produced manually by compressing the tablet which comprises both the pharmaceutically active ingredient and the gel forming polymer and placing it into a die which contain the granulation of the larger outer inert tablet and recompressing. In practice the die used to produce the final inlayed tablets must be at least 3/32 inch larger in diameter than the die used to produce the inner tablet. In general the die used to compress the final core is from about 1/32 inch to about 5/32 inch larger in diameter than the die used to produce the inner tablet.

Automated equipment, such as the Manesty Drycoater can be used to produce these tablets. This equipment is available from Thomas Engineering, Hoffman Estates, Ill. 60195 or Manesty Machines Limited, Evans Road, Speke, Liverpool L249LQ England.

Once the core is prepared, it can be coated and drilled in the manner described. Depending upon the rate and desired profile of delivery of the pharmaceutically active ingredient, holes may be placed in both faces of the device or in only one side. Similarly, it may be desirable to drill the holes so that only portions of the inner tablet face are exposed.

In the most preferred embodiment of the core of this invention, a two layer core is utilized. In this embodiment, which is shown in FIG. 4, one layer (30) comprises the pharmaceutically active ingredient and the gel forming polymer, while the inert layer (31) comprises the gel forming polymer and no pharmaceutically active ingredient. These cores can be prepared by manually filling a die with the granulation containing the active ingredient, hand tamping this layer with a flat-faced punch or standard concave punch with preferably no more than 500 lbs. of compression force, using a carver Laboratory Press Model C or using a Stokes F Press Model 519-2. Next the inert granulation is filled into the die on top of the layer which contains the pharmaceutically active ingredient and compressed sufficiently to give a hard core which is then coated using the procedure which follows.

The two layer cores so produced, may be coated and drilled using any of the procedures described. However, if it is desired to have apertures on only one face of the device, some identification mechanism must be used so that the face which contains the pharmaceutically active ingredient can be distinguished during the drilling operation.

The faces are most easily distinguished by composition or color thereby enabling a detector to identify the proper face for the drilling operation. Such detectors for this purpose may use photoacoustic spectroscopy, infrared and near infrared spectroscopy, UV and visible spectroscopy, fluorescence spectroscopy, magnetometry or any other appropriate technique known to those skilled in analytical chemistry.

In instances where the pharmaceutically active ingredient, the gel forming polymer and polymer hydration modulating agent exhibit the desired release rate, stability, and manufacturing characteristics, there is no critical upper or lower limit as to the amount of pharmaceutically active ingredient that can be incorporated into a layer of the core. The ratio of drug to excipient is dictated by the desired time span and profile of release, and the pharmacological activity of the drug.

Generally the pharmaceutically active ingredient containing layer of the core will contain about 1% to about 50% by weight of a beneficial agent admixed with other solute(s). Representative of compositions of matter that can be released from the device and can function as a solute are, without limitation, those compositions as described.

The coating, applied to the core of the invention, is a material that is impermeable and insoluble in the environment of use, can form films, and does not adversely affect the pharmaceutically active ingredient, animal body, or host. The coating is impermeable to water and also impermeable to the selected product, drugs, polymer hydration modulating agents, or to other compounds in the device. This impermeable material is insoluble in body fluids and non-erodible or it can be bioerodible after a predetermined period with bioerosion following the end of the active drug release period. In each instance it is impermeable to solvent and solute(s) found in the environment of use and is suitable for construction of the device.

The polymeric coating is applied to and adheres to the entire surface of the core. Apertures are cut in the coating to expose the core, using either a mechanical or laser drill, a coring device or any other pharmaceutically accepted means. In one embodiment, a mechanical drill is used to produce the apertures. In another embodiment, a laser is used to make the apertures.

The apertures allow solution to make contact only with exposed portions of the core when in use. The number, size and configuration of the apertures is chosen to provide the release rate required to suit a pharmacologically recognized requirement since the hydration of the polymer will occur only where the apertures allow such core-solvent contact.

The coating can be applied by dipping the cores into a suitable solution of the polymer or by spray coating the cores with the polymeric solution. Among the polymers that can provide this type of protection are cellulose acetate butyrate and polyvinyl chloride. In addition, other materials such as plasticizers may be included with the coating to enhance its stability, color, elasticity, ease of application or opacity, provided that these ingredients do not reduce the impermeability or insolubility of the coating. Similarly, compounds such as triethylcitrate may be added to the coating.

The coating is applied to a thickness of from about 1 to about 1000 microns but preferably about 10 to about 500 microns typically, although thinner and thicker coatings fall within the scope of the invention.

The expression "aperture" as used herein, refers to ports through the coating which expose the surface of the core to the environment. The size and number of apertures is chosen to effect the desired release rate. In determining the aperture size and number, the hydration rate of the gel forming polymer, the type and concentration of the polymer hydration modulating agent used in the core and the ability of the beneficial agent to form ions must be considered. The apertures are generally positioned in a regular pattern on both faces of the device although they can be positioned any where on the core including the edges or as previously described, on one face. The apertures are generally circular but may be of any design that results in the proper release rate. When the aperture is circular, its diameter ranges from about 0.1 mm to about 5 mm with diameters of about 0.3 to about 3.5 mm typical.

One embodiment of the impermeable wall includes a mixture of eight parts by weight of cellulose acetate butyrate, two parts by weight of cellulose acetate and one part by weight of diethylphthalate. This mixture is dissolved in a solution of methylene chloride and methanol (3:1 v/v) and sprayed onto the cores to a thickness of about 250 microns. Another preferred coating consists of five parts by weight of cellulose acetate butyrate and one part by weight of triethyl citrate dissolved in a mixture of acetone and methanol (3:1 v/v). This mixture is sprayed on the core or the cores are dipped into the mixture so that a coating of about 100 microns is applied.

In a preferred embodiment of the impermeable wall a mixture of ten parts by weight of cellulose acetate butyrate and one part by weight of triethylcitrate is used. This mixture at 3% w/v is dissolved in a solution of acetone and ethanol (3:1 v/v) or methylene chloride and methanol (3:1 v/v) and sprayed onto the cores to a thickness of about 100 microns.

The polymers used in the coating which are herein described are known to the art or can be prepared according to the procedures in the *Encyclopedia of Polymer Science and Technology*, Vol. 3, published by Interscience Publishers, Inc., N.Y., in *Handbook of Common Polymers* by Scott, J. R. and Roff, W. J., 1971, published by CRC Press, Cleveland, Ohio.

The following examples illustrate the preparation of the drug delivery device of this invention and their controlled release of one or more therapeutically active ingredients into an environment of use and as such are not to be considered as limiting the invention set forth in the claims appended hereto.

EXAMPLES

EXAMPLE 1

Two layered cores, where one layer contained a pharmaceutically active ingredient and a polymer which upon hydration forms microscopic gelatinous beads and a second layer which did not contain the pharmaceutically active ingredient were investigated as a means to improve the extent of delivery of a single layer core which contained the pharmaceutically active ingredient and polymer. The layer which contained the pharmaceutically active ingredient was twice the weight of the inert layer. The pharmaceutically active ingredient layer contained lovastatin, (40 mg/layer), CARBOPOL 974P (16 mg/layer), trisodium citrate (32 mg/layer), lactose (16 mg/layer). The inert layer contained AVICEL PH101 (20 mg/layer), CARBOPOL 974P (8 mg/layer), trisodium citrate (16 mg/layer) and lactose (8 mg/layer). The cores were coated with the impermeable wall a mixture of twenty parts by weight of cellulose acetate butyrate and three parts by weight of triethylcitrate. This mixture, at 3% w/v, was dissolved in a solution of acetone and ethanol (3:1 v/v) and sprayed onto the cores to a thickness of about 100 microns, using a Freund Model HCT-Mini Hi-Coater (pan).

Two hole configurations were evaluated: 39×0.5 mm holes drilled in the face of the device (See FIG. 5, #53) which allowed for exposure of the core layer which contained the pharmaceutically active ingredient, and 22×0.5 mm holes in the face of the device (See FIG. 5, #51) adjacent to the layer which contained the pharmaceutically active ingredient.

In vitro release rate performance of both sets of devices were measured at 37° C. in isotonic, phosphate buffer at pH 7.4 containing 0.4% w/w sodium dodecylsulfate using a USP Apparatus II at 50 rpm. The cumulative percent of lovastatin released was plotted against time and is shown in FIG. 5, using a single composition core devices with 39×0.5 mm holes (FIG. 5, #52) and 22×0.5 mm holes (FIG. 5, #51) as standards. As shown in FIG. 5, the release profiles for the two-layer device were significantly improved over the single composition core, in that in the last 20% of lovastatin was released at a more constant rate and greater than 95% of the lovastatin content was released in less than 20 hours. This is a 10–15% improvement in the cumulative percent released over the single composition core device.

EXAMPLE 2

Tablets for the controlled release of nifedipine were prepared from the following formulation:

|  | mg/Layer |
| --- | --- |
| Ingredients: Active Layer | |
| Nifedipine micronized | 33 |
| "CARBOPOL 974P" NF | 15 |
| Dibasic Sodium Phosphate (anhydrous)USP | 37.5 |
| Lactose Hydrous NF (spray dried) | 7.5 |
| Povidone USP K-90 | 2.5 |
| Magnesium Stearate NF | 0.5 |
|  | 96.0 |
| Ingredients: Inactive Layer | |
| AVICEL PH101 | 33 |
| "CARBOPOL 974P" NF | 15 |
| Sodium Citrate Dihydrate USP | 37.5 |
| Lactose Hydrous NF (impalpable) | 7.5 |
| Povidone USP K-90 | 2.5 |
| Magnesium Stearate NF | 0.5 |
|  | 96.0 |

The micronized nifedipine was combined with dibasic sodium phosphate, CARBOPOL, lactose and polyvinylpyrrolidone, mixed thoroughly then granulated using an aqueous alcoholic solvent blend (10% by volume water). The solvated mass was passed through a #20 screen then dried initially at 60° for two to four hours, then at 40° C. overnight. Magnesium stearate was sifted over the dried granulation and the total mixture passed through a #40 screen, The same procedure was used to prepare the inactive granulation with AVICEL substituted for nifedipine, The active granulation was filled into the 9/32" standard concave round die first and compressed with a force of 200–800 lbs then the inactive granulation was filled onto the lightly compressed active layer and the two layers compressed together with a force of 1500–2000 lbs. The resulting thickness was 4.3 mm and hardness was 18 kg. The tablets were coated to a thickness of 100 microns with the following coating formulation using a Uniglat Fluidized bed column spray coater.

| Film Coating Ingredients | Amount |
| --- | --- |
| Cellulose Acetate Butyrate (Eastman 381-20) | 140 g |
| Triethyl Citrate NF | 14 g |
| Methylene Chloride | 3000 ml |
| Alcohol USP | 1000 ml |

The tablets were mechanically drilled with 16×0.45 mm diameter openings through the coating on the active face.

Figure 6:
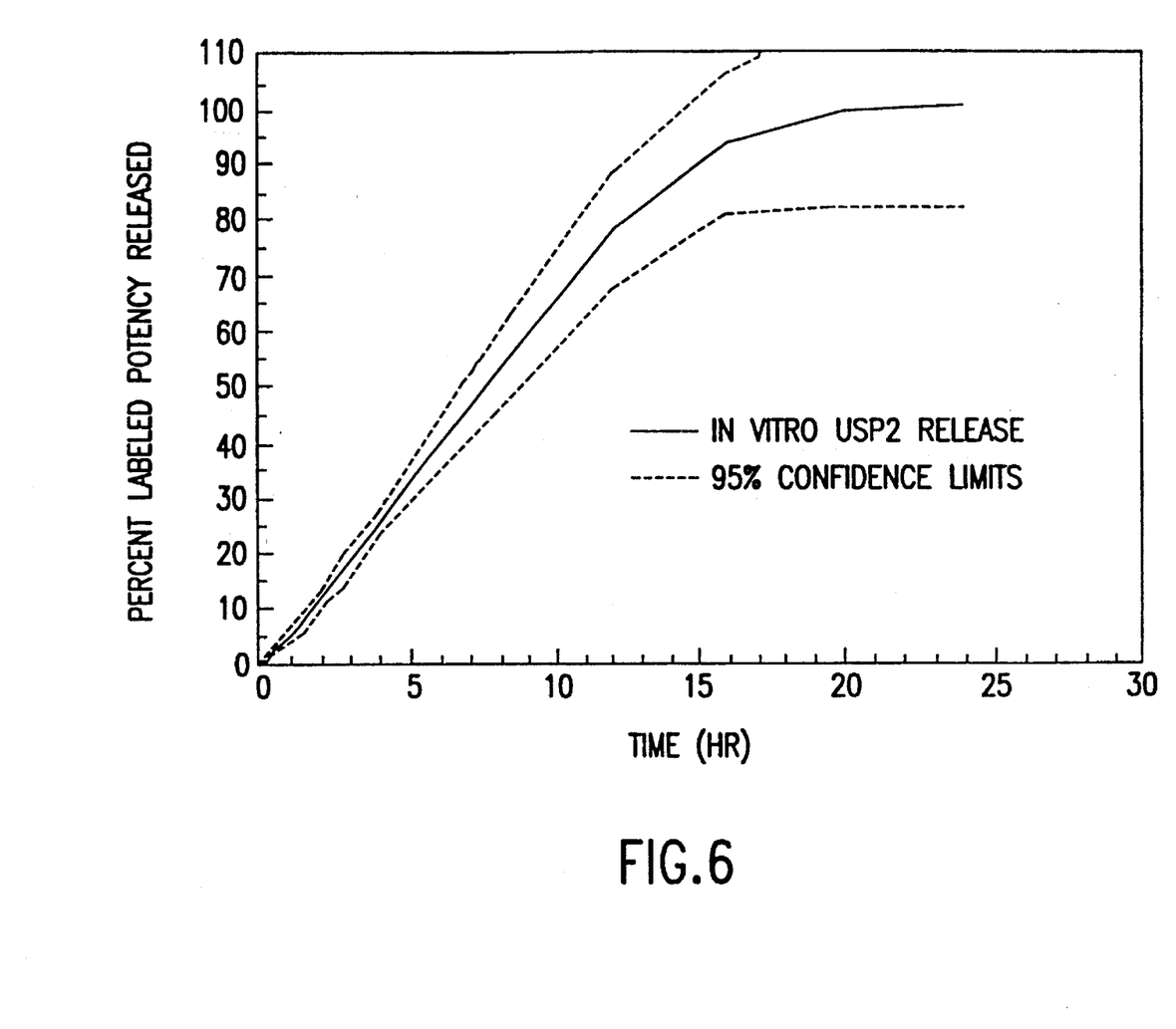
FIG. 6 shows the release profile for the composition of example 2.

In vitro release tests were carried out at 37° C. using USP Apparatus 2 into pH 7.4 phosphate buffer containing 2% sodium dodecyl sulfate at 100 rpm. The drug released was monitored by flow-through UV spectrophotometry at 340 nm. The results of this study are shown in FIG. 6. Two or three tablets can be filled into a gelatin capsule to provide 60 or 90 mg dosages.

What is claimed is:

1. A drug delivery device for the controlled in situ production and release of a suspension containing a beneficial agent, consisting of:

(a) a compressed core which comprises at least two layers, wherein at least one layer comprises an admixture of a therapeutically effective amount for those in need thereof, of a pharmaceutically active ingredient and a polymer which upon hydration forms microscopic polymer gel beads selected from the group consisting of sodium acrylate polymers and carboxypolymethylenes prepared from acrylic acid cross-linked with allyl ethers of sucrose or pentaerythritol; and at least one other layer comprising a polymer which upon hydration forms microscopic polymer gel beads; and (b) a water insoluble, water impermeable coating applied to the core, comprising a polymer and a plasticizer, which surrounds and adheres to the core, the polymer being selected from the group consisting of polyvinyl chloride, cellulose acetate, cellulose acetate butyrate or ethylcellulose, or combinations of these polymers, the plasticizer being selected from the group consisting of dibutylsebacate or triethylcitrate, the coating having apertures, exposing between about 5 and about 75% of the core surface.

2. The device of claim 1 wherein the polymer of the compressed core is selected from carboxypolymethylenes prepared from acrylic acid cross-linked with allyl ethers of sucrose or penterythritol and the pharmaceutically acceptable salts thereof.

3. The device of claim 1 wherein the amount of beneficial agent in the core comprises from about 1% to about 75% by weight of the core mixture.

4. The device of claim 1 wherein the beneficial agent is an HMG CoA reductase inhibitor.

5. The device of claim 4 wherein the beneficial agent is chosen from the group consisting of lovastatin, pravastatin and simvastatin.

6. The device of claim 1 wherein the beneficial agent is lovastatin.

7. The device of claim 1 wherein the beneficial agent is nifedipine.

8. The device of claim 1 wherein the amount of polymer, which upon hydration produces polymer gel beads in the core comprises from about 75% to about 10% by weight of the core mixture.

9. The device of claim 1, wherein the core mixture further comprises a polymer hydration modulating agent selected from the group consisting of acids, bases, salts sugars, surfactants and soluble polymers.

10. The device of claim 9, wherein the polymer hydration modulating agent is selected from the group consisting of sodium citrate, betamine hydrochloride, sodium bicarbonate, sodium carbonate and arginine.

11. The device of claim 1 wherein the insoluble, impermeable coating is selected from polyvinyl chloride, cellulose acetate, cellulose acetate butyrate or ethylcellulose.

12. The device of claim 1 wherein the apertures in the coating range in diameter from about 0.5 mm to about 2 mm.

13. The device of claim 12 wherein the apertures are arranged in an irregular pattern about the surface of the device.

14. A drug delivery device of claim 1, for the controlled in situ production and release of a suspension containing nifedipine, consisting essentially of:

(a) a compressed core comprising a first layer and a second layer, the first layer comprising a therapeutically effective amount for those in need thereof, of a pharmaceutically active ingredient and a polymer which forms polymer gel beads upon hydration, the polymer selected from the group consisting of sodium acrylate polymers and carboxypolymethylenes prepared from acrylic acid cross-linked with allyl ethers of sucrose or pentaerythritol; and a second layer comprising a polymer which forms polymer gel beads upon hydration; and (b) an insoluble, impermeable coating which surrounds and adheres to the core comprising a polymer and a plasticizer, the polymer being selected from the group consisting of polyvinyl chloride, cellulose acetate, cellulose acetate butyrate or ethylcellulose or combinations of these polymers, the plasticizer being selected from the group consisting of dibutylsebacate or triethylcitrate, the coating containing apertures which expose between about 10% and about 75% of the core surface.

15. The drag delivery device of claim 14, wherein the polymer is a carboxypolymethylenes prepared from acrylic acid cross-linked with allyl ethers of sucrose or penterythritol.

16. The drag delivery device of claim 14, wherein the insoluble, impermeable coating comprises cellulose acetate butyrate and triethylcitrate.

17. The drug delivery device of claim 14 which is in the form of a biconvex tablet, each convex side of the tablet being a face, each face having at least two apertures drilled through the coating to expose a portion of the core surface to the environment of use.

18. The drug delivery device of claim 17, wherein the apertures are drilled into only one face.

19. The drug delivery device of claim 18, wherein from about 10 to about 60 apertures are drilled into one face.

20. A process for the preparation of the device of claim 1 for the controlled release of an active agent wherein:

(a) the layers of the core are prepared separately by dry mixing or wet granulating the polymer which upon hydration produces polymer gel beads and granulating excipients, and dry mixing or wet granulating the pharmaceutically active ingredient with the polymer which upon hydration produces gelatinous microscopic beads and required excipients;

(b) compressing the mixtures into the appropriate layered-cores;

(c) applying the coating by either submersing the entire core into or spray coating the entire core with a suspension of the coating material; and (d) drilling apertures through the coating to expose the desired core surface area.

21. The process of claim 20, wherein the pharmaceutically active ingredient is nifedipine.

22. The process of claim 20, wherein the pharmaceutically active ingredient is lovastatin.

23. The process of claim 20, wherein the pharmaceutically active ingredient is simvastatin.

* * * * *